(12) United States Patent
Karpiel

(10) Patent No.: US 9,468,743 B2
(45) Date of Patent: Oct. 18, 2016

(54) CATHETER FOR POSITIONING A WIRE GUIDE

(71) Applicant: Cook Medical Technologies LLC, Bloomington, IN (US)

(72) Inventor: John A. Karpiel, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 116 days.

(21) Appl. No.: 13/743,705

(22) Filed: Jan. 17, 2013

(65) Prior Publication Data

US 2013/0197476 A1 Aug. 1, 2013

Related U.S. Application Data

(60) Provisional application No. 61/591,076, filed on Jan. 26, 2012.

(51) Int. Cl.
*A61M 25/00* (2006.01)
*A61M 25/09* (2006.01)

(52) U.S. Cl.
CPC ..... *A61M 25/09041* (2013.01); *A61M 25/007* (2013.01); *A61M 25/09* (2013.01); *A61M 2025/09175* (2013.01)

(58) Field of Classification Search
CPC ............ A61M 25/09041; A61M 2025/09916; A61M 2025/09175
USPC ....................................................... 600/585
See application file for complete search history.

(56) References Cited

U.S. PATENT DOCUMENTS

| | | | | |
|---|---|---|---|---|
| 2,856,934 A | * | 10/1958 | Petillo | 604/170.01 |
| 3,924,633 A | * | 12/1975 | Cook et al. | 604/104 |
| 4,405,314 A | | 9/1983 | Cope | |
| 4,581,017 A | * | 4/1986 | Sahota | 604/101.01 |
| 4,769,005 A | * | 9/1988 | Ginsburg | A61M 25/01 604/164.13 |

(Continued)

FOREIGN PATENT DOCUMENTS

WO WO 2005/049125 A1 6/2005

OTHER PUBLICATIONS

International Search Report for International Application No. PCT/US2013/021651 mailed Apr. 4, 2013.

(Continued)

*Primary Examiner* — Sean Dougherty
(74) *Attorney, Agent, or Firm* — Brinks Gilson & Lione

(57) ABSTRACT

A system and a method of positioning a wire guide are provided. The method includes inserting a wire guide in a first configuration into a lumen of a catheter, distally advancing the wire guide to a distal portion of the lumen so that a distal end of the wire guide is distal to an opening in a wall of the catheter and advancing a distal portion of the wire guide through the opening by distally advancing the distal portion relative to the catheter so that the distal end remains in the lumen as the distal portion of the wire guide extends out of the opening. The method includes advancing the distal portion of the wire guide further out of the opening so that the distal end exits through the opening so that the distal portion is distal to the distal end of the wire guide in a second configuration.

7 Claims, 6 Drawing Sheets

(56) References Cited

U.S. PATENT DOCUMENTS

| | | | |
|---|---|---|---|
| 5,263,938 A * | 11/1993 | Orr et al. .................... 604/171 |
| 5,290,229 A | 3/1994 | Paskar |
| 5,304,131 A | 4/1994 | Paskar |
| 5,499,991 A * | 3/1996 | Garman ............. A61B 17/0483 606/148 |
| 5,601,582 A * | 2/1997 | Shelton ............ A61B 17/32056 604/22 |
| 5,817,112 A * | 10/1998 | Christoudias ...... A61B 17/0469 606/139 |
| 6,071,292 A * | 6/2000 | Makower et al. ............ 606/158 |
| 6,902,555 B2 | 6/2005 | Paskar |
| 7,004,173 B2 * | 2/2006 | Sparks et al. ................. 128/898 |
| 7,347,863 B2 * | 3/2008 | Rothe ................ A61B 1/0014 606/139 |
| 8,556,916 B2 * | 10/2013 | Torrie ............... A61B 17/0469 606/148 |
| 2003/0236443 A1 * | 12/2003 | Cespedes ................ A61B 5/01 600/29 |
| 2004/0006306 A1 * | 1/2004 | Evans .................... A61B 17/22 604/101.03 |
| 2004/0242990 A1 * | 12/2004 | Brister et al. ................. 600/407 |
| 2007/0208302 A1 * | 9/2007 | Webster ............ A61M 25/0041 604/103.04 |
| 2009/0005793 A1 * | 1/2009 | Pantages ........... A61B 17/0057 606/144 |
| 2010/0305517 A1 | 12/2010 | Horie et al. |
| 2011/0004060 A1 | 1/2011 | Honda et al. |

OTHER PUBLICATIONS

Written Opinion for International Application No. PCT/US2013/021651 mailed Apr. 4, 2013.

* cited by examiner

CATHETER FOR POSITIONING A WIRE GUIDE

RELATED APPLICATIONS

This application claims the benefit of U.S. Provisional Application No. 61/591,076, filed Jan. 26, 2012, which is incorporated by reference herein in its entirety.

FIELD OF THE INVENTION

The present invention relates to wire guides used in the placement of medical devices, and more particularly to a catheter for positioning wire guides.

BACKGROUND OF THE INVENTION

Wire guides are elongate flexible members used to provide a path along which another medical device can be moved. The path provided by the wire guide can be used to navigate another medical device, such as a catheter through a body vessel. The use of wire guides to define such a path is known in the art. Briefly, a wire guide is navigated through a body lumen toward a point of treatment. Once positioned within the lumen, a therapeutic or diagnostic device, (i.e., a catheter) may be advanced over the wire guide to the target site and the desired therapeutic or diagnostic steps may be performed. The wire guide provides an established path for placing other devices and eliminates the need for performing delicate navigation procedures for each device passed into the body lumen, for example when additional procedures are performed. In some procedures, it is desirable to be able to withdraw the wire guide back through the catheter.

During placement of the wire guide, an operator must navigate the wire guide through a tortuous pathway in the body lumen due to the presence of natural bends and/or curves, or unnatural impediments, such as tumors, build-ups, and/or strictures. The presence of a tortuous path may make navigation of a wire guide through the path difficult, for example, the tip of the wire guide may get bent away from the desired path or caught in a stricture, or in some cases even perforate the wall of the lumen, etc. making further navigation into the lumen difficult or impossible.

The art contains many examples of wire guides having straight, flexible tips intended to aid in navigation of tortuous body lumens. The presence of a straight tip that is advanced tip forward, however, may make navigation more difficult. For example, upon encountering an impediment, the advancing tip may bend (reflex) into the lumen wall and become caught. Contact of the advancing tip with the lumen wall may prevent the wire guide from advancing further into the lumen as well as possibly damaging the lumen wall.

What is needed is a device for positioning a wire guide for navigating a tortuous body lumen and which addresses the other deficiencies described above, but which is still readily retractable into a catheter.

BRIEF SUMMARY

Accordingly, it is an object of the present invention to provide a device and a method having features that resolve or improve on the above-described drawbacks.

A method of positioning a wire guide for advancement through a lumen is provided. The method includes inserting a wire guide in a first configuration into a lumen of a catheter and distally advancing the wire guide to a distal portion of the lumen so that a distal end of the wire guide is distal to an opening in a wall of the catheter. The opening is positioned proximal to a distal end of the catheter. The method also includes advancing a distal portion of the wire guide through the opening by distally advancing the distal portion of the wire guide relative to the catheter so that the distal end of the wire guide remains in the lumen as the distal portion of the wire guide extends out of the opening. The distal portion is proximal to the distal end in the first configuration. The method includes advancing the distal portion of the wire guide further out of the opening so that the distal end of the wire guide exits through the opening such that the distal portion of the wire guide is distal to the distal end of the wire guide in a second configuration.

In another aspect, a system for is provided for positioning a wire guide for advancement through a lumen. The system includes a catheter having a proximal portion, a distal portion and a lumen extending at least through the distal portion of the catheter. The catheter also includes an opening in a wall of the distal portion of the catheter, the opening having a proximal end and a distal end where the lumen extends distal to the distal end of the opening. The system also includes a wire guide having a proximal portion, a distal portion, and a distal end distal to the distal portion. The wire guide is advanceable into the lumen in a first configuration and positionable in a second configuration by advancing the distal portion through the catheter opening so that the distal end of the wire guide is proximal to the distal portion of the wire guide in the second configuration.

DETAILED DESCRIPTION

Figure 1:
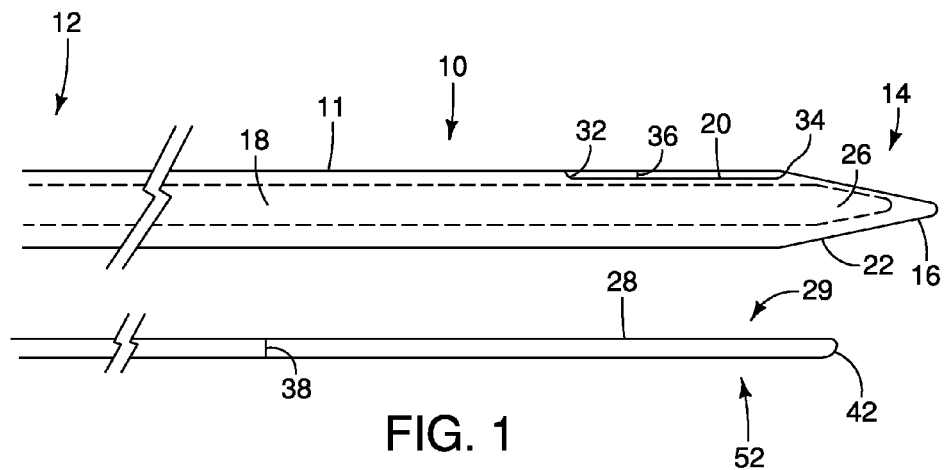
FIG. 1 is a partial side view of a catheter and a wire guide in accordance with an embodiment of the present invention.
Figure 2:
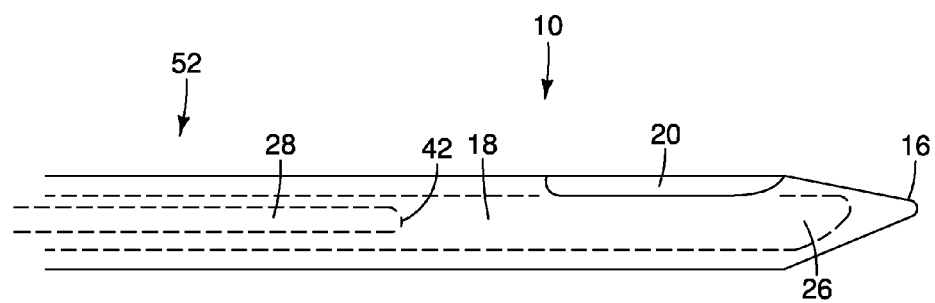
FIG. 2 is a partial side view of an embodiment of the catheter and the wire shown in FIG. 1 in a first configuration.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering a medical device to a patient. Hence the term "distal" means the portion of the catheter that is farthest from the physician and the term "proximal" means the portion of the catheter that is nearest to the physician.

Figure 11:
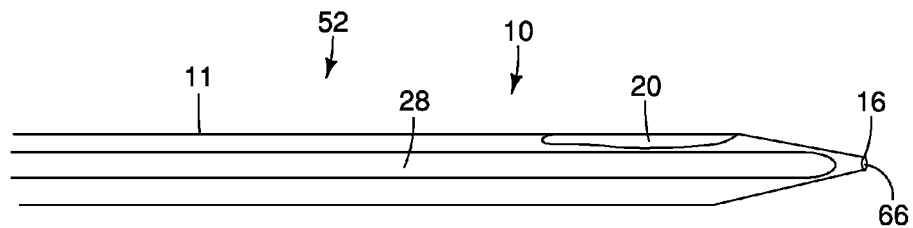
FIG. 11 is a partial side view of an alternative embodiment of a catheter and a wire guide in accordance with an embodiment of the present invention.

FIG. 1 illustrates a catheter 10 in accordance with an embodiment of the present invention. The catheter 10 includes an elongate body 11 having a proximal portion 12 and a distal portion 14. A distal end 16 of the distal portion 14 of the catheter 10 may be closed as shown in FIG. 1. In some embodiments, the distal end 16 may have an opening sized to allow fluids to enter and exit the distal end 16, but the opening does not allow devices to pass through the distal end 16. (See FIG. 11, showing an opening 66.) At least one lumen 18 extends through the catheter 10 from the proximal portion 12 to the distal portion 14. In the embodiments having the opening 66 at the distal end 16, the opening 66 may connect to the lumen 18. Additional lumens may also be included in the catheter 10. The distal portion 14 may include a tapered outer wall 22 extending to the distal end 16.

Figure 12:
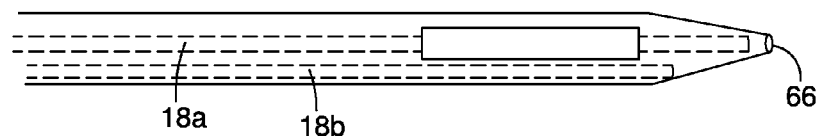
FIG. 12 is a partial top view of an alternative embodiment of a catheter in accordance with an embodiment of the present invention.

The catheter 10 further includes an opening 20 formed in the distal portion 14 of the catheter 10. The opening 20 is proximal to the distal end 16 of the catheter 10. The opening 20 is connected to the lumen 18 of the catheter 10. A distal portion 26 of the lumen 18 extends distal to a distal end 34 of the opening 20. In some embodiments, the distal portion 26 of the lumen 18 extending distal to the distal end 34 may be about 1 mm to about 2 mm. In some embodiments other lengths for the distal portion 26 of the lumen 18 may be used. In some embodiments, the opening 20 has an elongated oval shape. Other shapes for the opening 20 are also possible. In some embodiments, a proximal end 32 or the distal end 34 or both ends 32, 34 of the opening 20 may be straight or curved. (See also FIG. 12.) As shown in FIG. 12, the length of the opening 20 is typically greater than the width of the opening 20. In some embodiments, the opening 20 may have a width 36 that is slightly wider than a diameter 38 of the wire guide 28 that may be positioned using the catheter 10. The distal end 34 is sized and shaped such that a wire guide 28 can contact the distal end 34 of the opening 20 and move past the distal end 34 without getting stuck in the distal end 34 of the opening 20. In some embodiments, the length of the opening 20 is at least about 1 cm. In some embodiments, the length of the opening may be about 2 cm to about 3 cm. Although, some embodiments may be other lengths. The wire guide 28 is shown external to the catheter 10 in FIG. 1. The catheter 10 and the wire guide 28 may be formed from any materials suitable for use in patients known to one skilled in the art.

FIGS. 2-10 illustrate the positioning of wire guide 28 using the catheter 10. The wire guide 28 may be any kind of wire guide known in the art that is used for navigation through bodily lumens and for delivering medical devices over the wire guide. The wire guide 28 may include a more flexible distal tip portion 29 relative to the proximal portion to facilitate positioning of the wire guide. In some embodiments, the distal tip portion 29 of the wire guide 28 may be about 4 mm to about 8 mm and in some embodiments about 6 mm. Other lengths of the flexible distal end 29 may also be used and typically the flexibility and the length of the flexible tip will depend on the location to which the wire guide must travel through a body lumen. The wire guide 28 may be any diameter. The size of the opening 20 of the catheter 10 may be configured based on the diameter and the flexibility of the wire guide 28. In some embodiments, the length of the opening 20 may be determined based on the flexibility of the wire guide 28 such that the opening allows the wire guide 28 to bend and reposition a distal end 42 of the wire guide 28 relative to the remainder of the wire guide 28.

Figure 3:
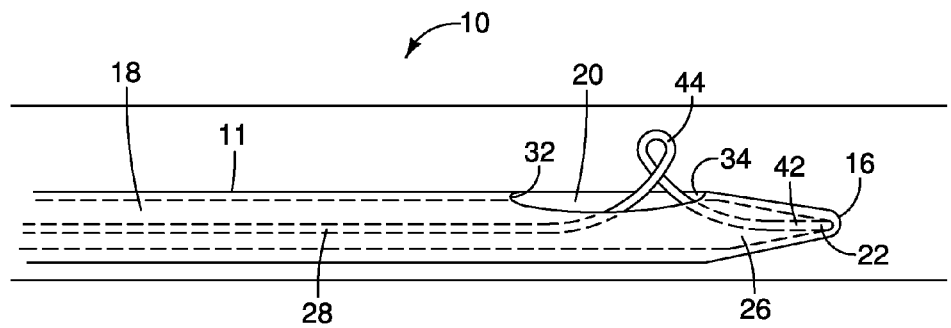
FIG. 3 is a partial side view of an embodiment of the catheter and the wire shown in FIG. 1.
Figure 13:
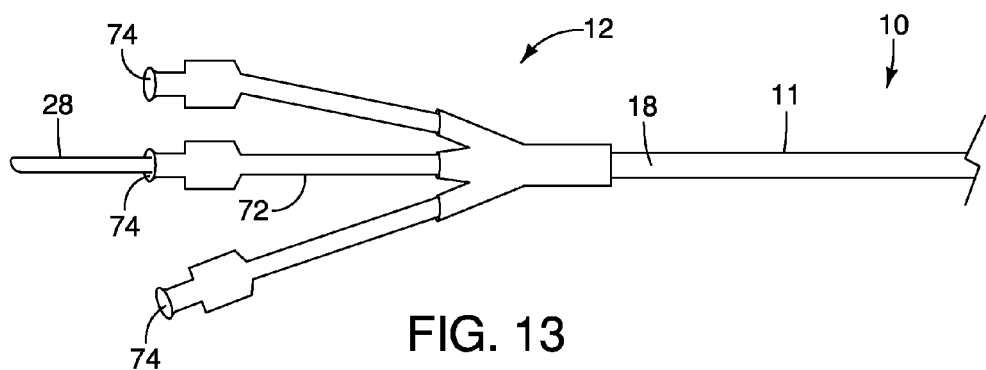
FIG. 13 is a partial view of a proximal portion of a catheter and a wire guide in accordance with an embodiment of the present invention.

The wire guide 28 may be inserted through a tube 72 in the proximal portion 12 of the catheter 10 connected to the lumen 18 (see for example FIG. 13) and extended toward the closed distal end 16 of the catheter 10. The proximal portion 12 of the catheter 10 illustrated in FIG. 13 shows three entry ports 74; however, the catheter may include one, two or more entry ports 74. The wire guide 28 is shown being inserted into the lumen 18 of the catheter 10 in FIG. 2 with the distal end 42 of the wire guide 28 being advanced toward the distal portion 26 of the lumen 18. The wire guide 28 is in a first, substantially straight configuration 52. As shown in FIG. 3, the distal end 42 of the wire guide 28 is shown extended into the distal portion 26 of the lumen 18 of the catheter 10 and distal to the distal end 34 of the opening 20. In some embodiments, the wire guide 28 may be inserted into the lumen 18 until the distal end 42 of the wire guide 28 contacts the distal end 16 of the body 11. In some embodiments, the distal portion 26 of the lumen 18 may be tapered so that the wire guide 28 is prevented from extending to the distal end 16 of the catheter 10 but still extends distal to the distal end 34 of the opening 20.

As shown in FIG. 3, the distal end 42 of the wire guide 28 may be extended to the distal portion 26 of the lumen 18 and distal to the distal end 34 of the opening 20. The distal end 42 may be extended distally so that the distal end 42 of the wire guide 28 contacts the distal end 16 of the catheter 10. The wire guide 28 may be further advanced distally so that a distal portion 44 of the wire guide 28 proximal to the distal end 42 bends and extends out of the opening 20 while the distal end 42 of the wire guide 28 is positioned in the distal portion 26 of the lumen 18 of the catheter 10. As the wire guide 28 is further advanced distally and the distal end 42 remains within the lumen 18 of the catheter 10, the distal portion 44 of the wire guide 28 begins to flip or bend as the distal portion 44 extends further out of the opening 20. (See FIGS. 4 and 5).

Figure 4:
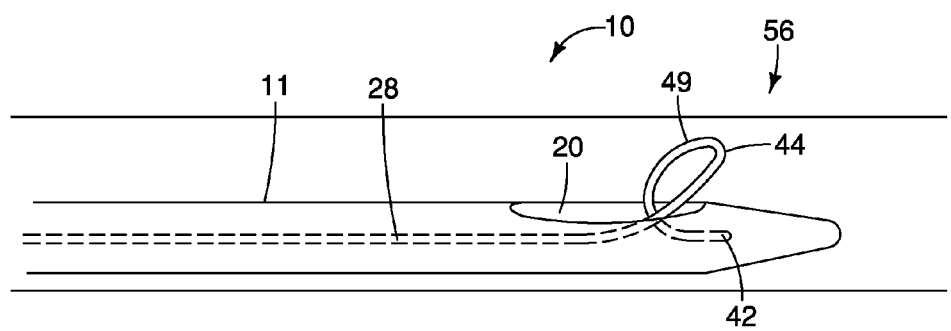
FIG. 4 is a partial side view of an embodiment of the catheter and the wire shown in FIG. 1.
Figure 5:
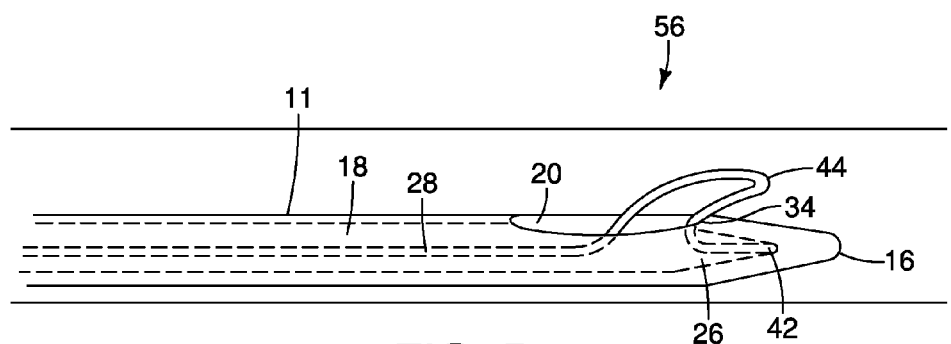
FIG. 5 is a partial side view of an embodiment of the catheter and the wire shown in FIG. 1.

As shown in FIG. 4, the distal portion 44 of the wire guide 28 is flipped over itself and forms an intermediate loop 49 as the distal portion 44 is pushed out of the opening 20 by distally moving the wire guide 28 relative to the catheter 10. The distal end 16 of the catheter 10 prevents the distal end 42 of the wire guide 28 from distally advancing so that the distal portion 44 is advanced out of the opening 20. FIG. 5 illustrates the distal portion 44 of the wire guide 28 bending as the distal portion 44 contacts the distal end 34 of the opening 20 and the distal end 42 remains positioned within the distal end 16 of the catheter 10 position with the remainder of the wire guide 28 is advanced distally. The distal portion 44 of the wire guide 28 is extendable out through the opening 20 of the catheter 10 to facilitate positioning the wire guide 28 from the first, straight configuration 52 to a second, bent configuration 54 where the distal end 42 of the wire guide 28 extends proximally toward a proximal portion 45 of the wire guide 28 (see FIG. 8).

Figure 6:
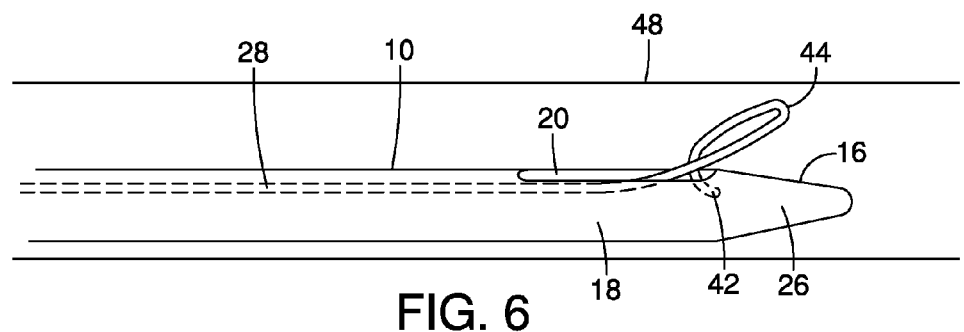
FIG. 6 is a partial side view of an embodiment of the catheter and the wire shown in FIG. 1.
Figure 7:
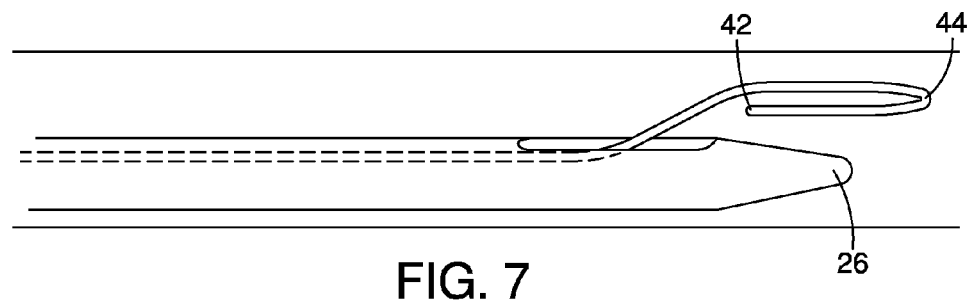
FIG. 7 is a partial side view of an embodiment of the catheter and the wire shown in FIG. 1 in a second configuration.

As shown in FIG. 6, the distal portion 44 extends distally out of the opening 20 of the catheter 10 and is advanced distally relative to the distal end 16 of the catheter 10 as the wire guide 28 is moved distally relative to the catheter 10. As the distal portion 44 of the wire guide 28 advances distally, the distal end 42 of the wire guide 28 moves away from the distal portion 26 of the lumen 18 and toward the opening 20. FIG. 7 illustrates the distal end 42 of the wire guide 28 that is extended out of the opening 20 of the catheter 10. The distal end 42 of the wire guide 28 is proximal to the distal portion 44 of the wire guide 28 in the second configuration 54.

Figure 8:
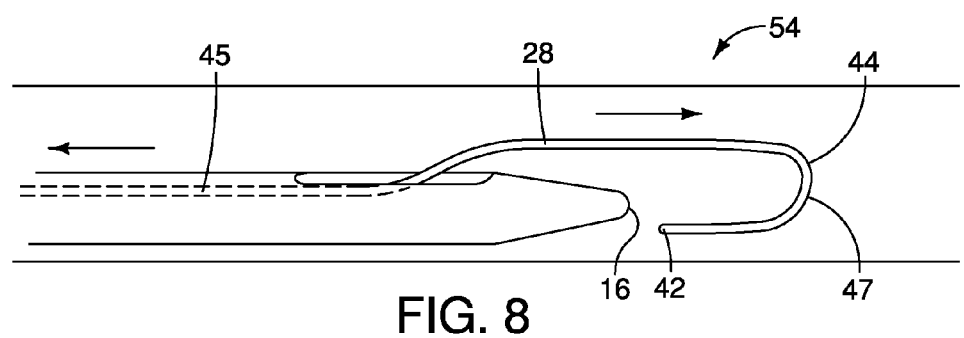
FIG. 8 is a partial side view of an embodiment of the catheter and the wire shown in FIG. 1 in the second configuration.
Figure 9A:
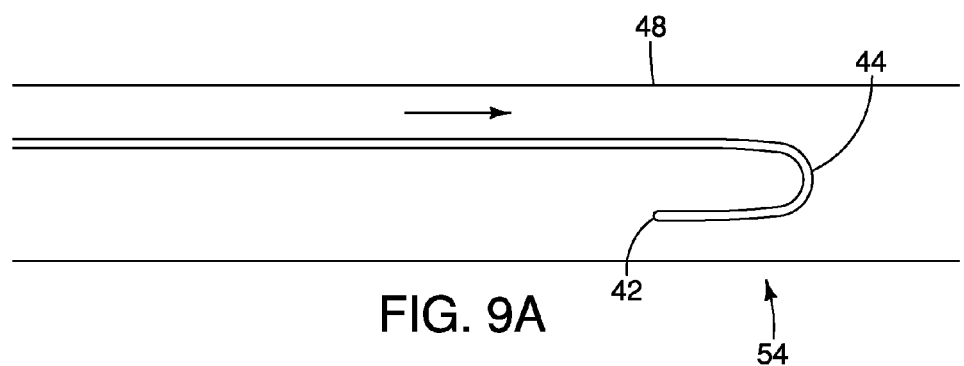
FIG. 9A is a partial side view of a wire guide in accordance with an embodiment of the present invention in a second configuration.
Figure 9B:
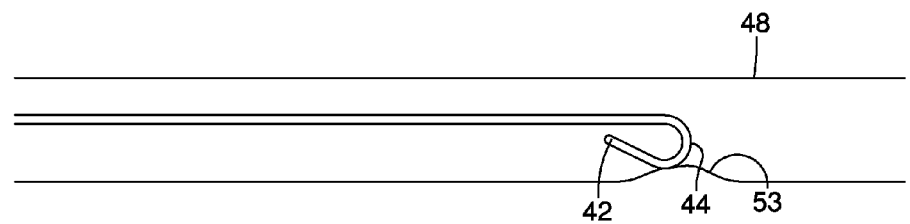
FIG. 9B is a partial side view of a wire guide in accordance with an embodiment of the present invention in a second configuration.
Figure 14:
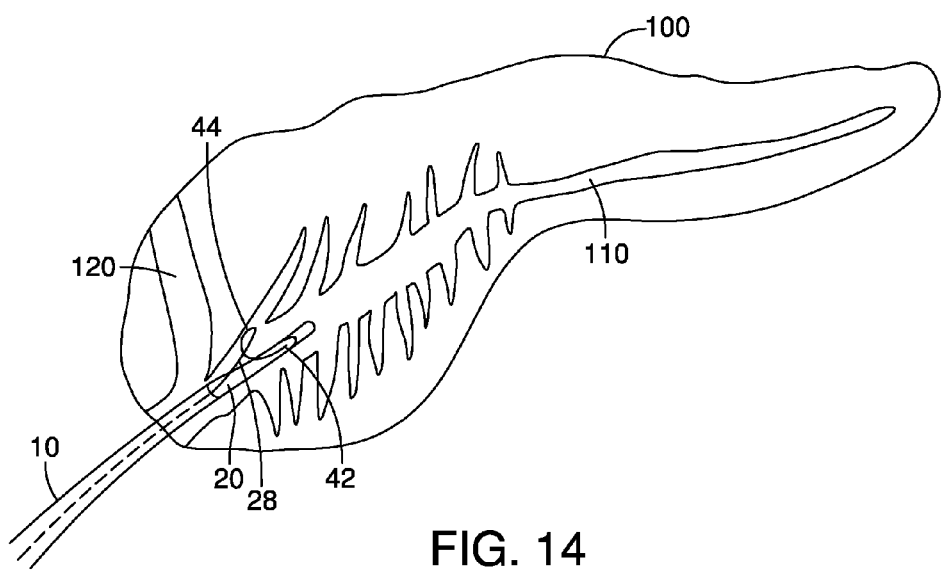
FIG. 14 is an illustration of the catheter and wire guide positioned within the pancreatic duct.

FIG. 8 illustrates the wire guide 28 in the second configuration 54 where the distal portion 44 of the wire guide 28 is advanced distally relative to the catheter 10. In some embodiments, the wire guide 28 may be advanced and in some embodiments, the catheter 10 may be proximally withdrawn so that the distal portion 44 and the distal tip 42 of the wire guide 28 are positioned distal to the distal end 16 of the catheter 10 as shown in FIG. 8. The distal portion 44 of the wire guide 28 may be extended and moved to the second configuration 54 within a body lumen or an endoscope channel. In some embodiments, the distal portion 44 may be pressed against a wall 48 of the body lumen or the endoscope channel the help facilitate the flipping of the distal end 42 to the second configuration 54. FIG. 14 illustrates the wire guide 28 and the catheter 10 positioned within the pancreatic duct 110 of the pancreas 100 where the distal portion 44 of the wire guide 28 has been distally advanced past the common bile duct 120 and is extended out of the opening 20 of the catheter 10. The distal end 42 flips from the first configuration 52 where the distal end 42 is the distal most portion of the wire guide 28 to the second configuration 54 where the distal portion 44 is distal to the distal end 42 of the wire guide 28 and the distal end 42 extends proximally to the proximal portion 45 of the wire guide 28. In the second configuration 54, the distal portion 44 is advanced distally ahead of the distal end 42 through the patient's lumen. The distal portion 44 provides a smooth, flexible surface 47 that facilitates advancement of the wire guide 28 through tortuous portions of the patient's lumen and avoids having the distal end 42 of the wire guide 28 getting caught in or piercing the lumen wall as the wire guide 28 is advanced distally as shown in FIGS. 9A and 9B. FIG. 9B illustrates the distal portion 44 of the wire guide 28 contacting a deformation 53 in the body lumen 48 and the distal portion 44 bending against the deformation 53 to continue advancing distally within the lumen 48.

Figure 10:
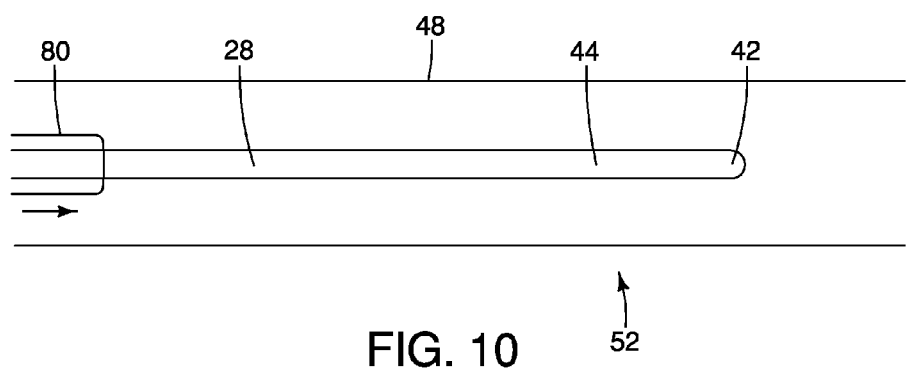
FIG. 10 is a partial side view of a wire guide and a medical device.

Once the wire guide 28 is delivered to the treatment site within the patient, the wire guide 28 may be proximally withdrawn to return the wire guide 28 to the first configuration 52 as shown in FIG. 10. Other medical devices 80 may be advanced over the wire guide 28 to the treatment site within the body lumen. In some embodiments, the medical device 80 may be used to return the wire guide 28 to the first configuration 52 by advancing the medical device 80 distally to the distal end 42 of the wire guide 28.

The wire guide 28 may be withdrawn from the treatment site once the medical device 80 has been positioned. In some procedures, the wire guide 28 may be re-advanced to the same treatment site or to another treatment site. The wire guide 28 may be returned to the second configuration 54 shown in FIG. 8 using the catheter 10. The wire guide 28 may be proximally withdrawn so that the distal end 42 of the wire guide 28 is positioned within the lumen 18 of catheter 10. The distal end 42 may then be advanced distally within the lumen 18 until the distal end 42 of the wire guide 28 is distal to the distal end 34 of the opening 20 and the procedure described above for moving the wire guide 28 from the first configuration to the second configuration may be repeated.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A system for positioning a wire guide for advancement through a lumen, the system comprising:
   a catheter comprising:
      a proximal portion;
      a distal portion;
      a lumen extending at least through the distal portion of the catheter;
      an opening in a wall of the distal portion of the catheter, the opening having a proximal end and a distal end, the lumen extending distal to the distal end of the opening; and
   a wire guide comprising:
      a proximal portion;
      a distal portion; and
      a distal end distal to the distal portion;
   wherein the wire guide is distally advanceable into the lumen in a first configuration, the distal end of the wire guide is distal to the distal portion of the wire guide in the first configuration; the wire guide being positionable in a second configuration by distally advancing the distal end of the wire guide to a distal end of the catheter lumen and advancing the distal portion through the catheter opening so that the distal portion advances through the catheter opening before the distal end so that the distal end of the wire guide is proximal to the distal portion of the wire guide in the second configuration as the distal portion is advanced distally and the distal end exits the catheter opening.

2. The system of claim 1, wherein the catheter comprises a closed distal end.

3. The system of claim 1, wherein the opening is oval or rectangular shaped.

4. The system of claim 1, wherein the catheter comprises a plurality of lumens.

5. The system of claim 1, wherein the distal tip has a greater flexibility relative to the proximal portion of the wire guide.

6. The system of claim 1, wherein the wire guide forms a loop in an intermediate position between the first configuration and the second configuration.

7. The system of claim 1, wherein the lumen is operably connected to a distal end opening having a diameter that is less than a diameter of the wire guide so that the wire guide cannot pass through the opening.

* * * * *